US012565879B2

(12) United States Patent
Felten et al.

(10) Patent No.: US 12,565,879 B2
(45) Date of Patent: Mar. 3, 2026

(54) VACUUM PUMP AND FACILITY FOR PROCESSING AND/OR PACKAGING FOOD PRODUCTS

(71) Applicant: Ateliers Busch SA, Chevenez (CH)

(72) Inventors: Nicolas Felten, Bourogne (FR); Erik Lippelt, Inzlingen (DE)

(73) Assignee: Ateliers Busch SA, Chevenez (CH)

( * ) Notice: Subject to any disclaimer, the term of this patent is extended or adjusted under 35 U.S.C. 154(b) by 0 days.

(21) Appl. No.: 18/833,438

(22) PCT Filed: Jan. 24, 2023

(86) PCT No.: PCT/EP2023/051595
§ 371 (c)(1),
(2) Date: Jul. 26, 2024

(87) PCT Pub. No.: WO2023/144102
PCT Pub. Date: Aug. 3, 2023

(65) Prior Publication Data
US 2025/0101970 A1 Mar. 27, 2025

(30) Foreign Application Priority Data

Jan. 26, 2022 (CH) ............................... 000077/2022

(51) Int. Cl.
*F04B 37/14* (2006.01)
*A61L 2/10* (2006.01)
*F04B 39/16* (2006.01)

(52) U.S. Cl.
CPC ................ *F04B 37/14* (2013.01); *A61L 2/10* (2013.01); *F04B 39/16* (2013.01)

(58) Field of Classification Search
CPC .......... F04B 37/14; F04B 39/16; F04B 41/06; A61L 2/10; A61L 2/04; A61L 2/16; F04C 25/02; F04C 18/344; F04C 29/0092; F04C 2220/10; F04D 19/04
See application file for complete search history.

(56) References Cited

U.S. PATENT DOCUMENTS

| | | | |
|---|---|---|---|
| 4,066,551 A * | 1/1978 | Stern .......................... | C02F 9/20 210/282 |
| 4,595,498 A * | 6/1986 | Cohen ....................... | C02F 9/00 210/257.2 |
| 4,993,598 A | 2/1991 | Groninger | |

(Continued)

FOREIGN PATENT DOCUMENTS

| | | |
|---|---|---|
| CN | 204957080 | 1/2016 |
| FR | 2968733 | 6/2012 |
| WO | 2018082877 | 5/2018 |

OTHER PUBLICATIONS

Written Opinion and International Search Report (with translation) for PCT/EP2023/051595, dated May 9, 2023, 12 pages.

*Primary Examiner* — Hoang M Nguyen
(74) *Attorney, Agent, or Firm* — Tucker Ellis LLP

(57) ABSTRACT

The invention relates to a vacuum pump (1), having a suction (11), a discharge (9) and an interior volume intended to be traversed by gases conveyed from the suction (11) to the discharge (9) by pumping by the vacuum pump. The vacuum pump (1) comprises at least one sterilization element (15) of at least a portion (18) of the interior volume. The invention also relates to an installation for processing and/or packaging food products.

13 Claims, 4 Drawing Sheets

(56)                    References Cited

U.S. PATENT DOCUMENTS

| 2010/0150775 | A1* | 6/2010 | Reddy | A61L 2/04 |
| | | | | 422/310 |
| 2015/0209457 | A1* | 7/2015 | Bonutti | A61L 2/10 |
| | | | | 250/435 |
| 2017/0014539 | A1 | 1/2017 | Min et al. | |
| 2021/0023250 | A1* | 1/2021 | Golkowski | C01B 15/01 |

* cited by examiner

VACUUM PUMP AND FACILITY FOR PROCESSING AND/OR PACKAGING FOOD PRODUCTS

TECHNICAL FIELD OF THE INVENTION

The present invention relates to vacuum technology. More specifically, it relates to a vacuum pump, as well as to an installation for processing and/or packaging food products.

STATE OF THE ART

Vacuum packaging of food is known. It is carried out in installations comprising a vacuum chamber that one or more connecting lines connect to one or more vacuum pumps. The function of the vacuum pump(s) is to produce and then maintain a vacuum in the vacuum chamber. In addition to the packaging of foodstuffs, the preparation of foodstuffs can be carried out in such a vacuum chamber.

The very low pressure in the vacuum chamber promotes the evaporation of liquids present in the food and/or their transformation into volatile aerosols. Substances from the foodstuffs can thus be sucked into the connection pipe(s) to the vacuum pump(s), especially in gaseous form or as aerosols. As a result, the connecting line(s) between the vacuum chamber and the vacuum pump(s) may become progressively contaminated with food material from the food in the vacuum chamber. There is a risk that pathogenic micro-organisms such as bacteria may develop in the connection line(s) between the vacuum chamber and the vacuum pump(s), which must be absolutely avoided for health reasons.

In order to prevent pathogenic micro-organisms such as bacteria from developing in the connection line(s) between the vacuum chamber and the vacuum pump(s), it is known to regularly disconnect and clean these connection lines, which requires a maintenance intervention and sometimes the temporary shutdown of the installation.

SUMMARY OF INVENTION

The purpose of the invention is at least to increase the sanitary safety in and/or around installations where a vacuum is produced by one or more vacuum pumps.

According to the invention, this is achieved by means of a vacuum pump which comprises a suction, a discharge, an internal volume intended to be traversed by the gases conveyed from the suction to the discharge by the pumping by the vacuum pump, as well as at least one element for sterilizing at least a portion of the internal volume.

The sterilization element may be a single sterilization element, or it may be one of several sterilization elements that the vacuum pump includes. The sterilization element(s) may be positioned in such a way as to sterilize a potential focus of microorganism growth and dissemination or a buffer zone between an upstream region that may be upstream of the pump suction and a downstream region that may be the surrounding atmosphere.

If the vacuum pump according to the invention is connected to a vacuum chamber via a connecting line, the risk of contamination of the vacuum chamber by microorganisms from the vacuum pump is reduced, in particular in the event that a scheduled cleaning of the connecting line is not carried out until after the originally planned date, is incorrectly carried out, or is omitted.

Advantageously, the interior volume comprises a buffer zone that can be sterilized by the sterilization element(s), this buffer zone comprising a passage for all the gases conveyed by the pumping by the vacuum pump.

The buffer zone can prevent upstream contamination by microorganisms present downstream of this buffer zone. Also, viruses, for example from foodstuffs in a vacuum chamber, can be destroyed in the buffer zone and thus not be expelled into the surrounding atmosphere by the vacuum pump's discharge.

Where provided, the entire buffer zone is sterilized. However, the sterilization of the entire buffer zone may be limited to one or more microorganisms and/or one or more viruses. In this sense, the sterilization of the entire buffer zone can be only partial. It can also be total by eliminating any microorganisms and/or viruses in the buffer zone.

Advantageously, the buffer zone extends to the suction of the vacuum pump.

When this is the case, the buffer zone can prevent contamination of the vacuum pump suction with microorganisms from occurring and then spreading downstream of the vacuum pump from the vacuum pump suction and reaching, for example, a vacuum chamber where food products are processed and/or vacuum packed.

Advantageously, the vacuum pump comprises at least one pumping chamber where the conveying of gases by the vacuum pump takes place, at least a part of the passage of the buffer zone being located upstream of the pumping chamber.

Advantageously, the vacuum pump comprises a filtering grid for the pumped gases, this grid being located upstream of the pumping chamber, at least part of the passage of the buffer zone being located upstream of the grid.

Advantageously, one upstream surface among two opposite main surfaces of the grid can be sterilized by the sterilization element or elements.

Advantageously, the sterilization element is an ultraviolet light source.

The one or more ultraviolet light sources produce ultraviolet light alone or ultraviolet light and one or more other lights. Advantageously, the one or more ultraviolet light sources produce ultraviolet light in a wavelength range from 250 nm to 280 nm. When this is the case, ultraviolet light has a very high efficiency in suppressing viruses such as rotavirus and several pathogenic bacteria including *Escherichia coli* and *Staphylococcus aureus*. More advantageously, the ultraviolet light source(s) produce ultraviolet light in a wavelength range from 260 nm to 270 nm. When this is the case, ultraviolet light has an even higher efficacy in suppressing viruses such as rotavirus and several pathogenic bacteria including *Escherichia coli* and *Staphylococcus aureus*.

Advantageously, the ultraviolet light source is one of several ultraviolet light sources included in the vacuum pump and which are able to illuminate together a whole portion of the inner wall delimiting and surrounding the passage of the buffer zone. In this way, this entire wall portion can be effectively disinfected and the buffer zone can effectively play its role as a barrier against microbial contamination between an area upstream of the buffer zone and an area downstream of the buffer zone.

Advantageously, the vacuum pump comprises an insert duct forming the suction of the vacuum pump, this insert duct being provided with the sterilization element. In this way, any standard pump can be converted into a pump according to the invention.

Advantageously, the sterilization element is a heating element. This heating element can perform heating by radiation, for example of the buffer zone. The heating element can also be an annular electrical resistance surrounding and delimiting the passage of the buffer zone.

Advantageously, the vacuum pump is a lubricated pump comprising a pumping chamber where the gases are conveyed by the vacuum pump, as well as lubricating oil present in particular in the pumping chamber, the lubricating oil being or comprising the sterilization element.

Advantageously, the sterilization element is or comprises an antiseptic chemical substance.

The invention also has the object of an installation for processing and/or packaging food products, which comprises a vacuum chamber and at least one vacuum pump as defined in the preceding, the suction of this vacuum pump being connected to the vacuum chamber.

BRIEF DESCRIPTION OF THE DRAWINGS

Further advantages and features will become clearer from the following description of several particular embodiments of the invention given as non-limiting examples and shown in the attached drawings, including.

DESCRIPTION OF A PREFERRED EMBODIMENT OF THE INVENTION

Figure 1:
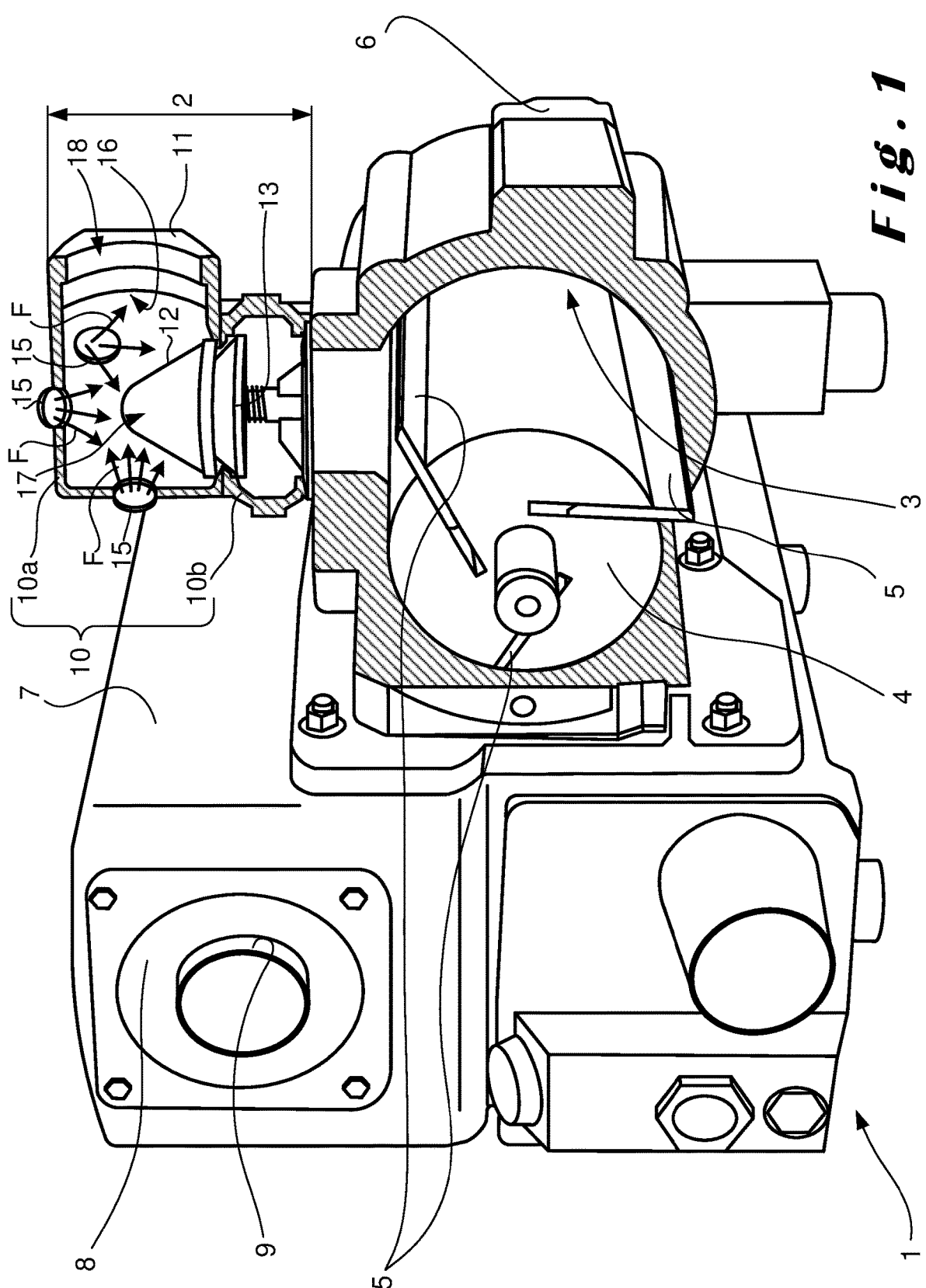
FIG. 1 is a pull-out perspective view of a vacuum pump according to a first embodiment of the invention.

In FIG. 1, a vacuum pump 1 according to a first embodiment of the invention is more specifically a lubricated vane pump. It comprises an upstream subassembly 2 and a pumping chamber 3, in which a rotor 4 provided with a plurality of vanes 5 is mounted so as to be rotatable. A motor 6 is provided to drive the rotor 4 in rotation.

The pumping chamber 3 communicates with an enclosure 7, the lower part of which forms a lubricating oil tank (not visible). In the upper part of the enclosure 7, an oil filter 8 is mounted, which is designed to extract the oil present in the pumped gases before these gases are evacuated, for example, into the atmosphere via the discharge 9 of the vacuum pump 1.

When the rotor 4 rotates on its axis, the vanes 5 pull the gases present in the pumping chamber 3 and expel them towards the enclosure 7. This generates a suction by the upstream subassembly 2.

Here, as in the appended claims, the terms "upstream" and "downstream" and the like refer to the direction in which the gases flow pumped by the vacuum pump 1.

The upstream subassembly 2 comprises an assembly of several successive parts 10a and 10b forming a duct 10, the upstream end of which is the suction 11 of the vacuum pump 1. The downstream end of the duct 10 communicates with the pump chamber 3. A grid 12 for filtering the sucked gases entering through the suction 11 is mounted in the duct 10. A non-return valve 13 is mounted downstream of the grid 12, in the duct 10.

The upstream subassembly 2 is placed upstream of the pumping chamber 3. In a particular embodiment of the invention, the upstream subassembly 2 is placed directly upstream of the pumping chamber 3.

The chamber 10a is provided with a plurality of sterilization elements, each of which is an ultraviolet light source 15. For example, each ultraviolet light source 15 may be an LED. The ultraviolet light sources 15 are arranged and directed so as to illuminate together the entire inner wall 16 of the chamber 10a, as well as the upstream surface 17 of the grid 12. The ultraviolet light beams emitted by the ultraviolet light sources 15 are symbolized by the arrows F in FIG. 1.

The area delimited by the chamber 10a is a buffer zone 18 that the ultraviolet light emitted by the ultraviolet light sources 15 sanitizes in its entirety by destroying any microorganisms present and any viruses present. The buffer zone 18 forms a passage through which all the gases pumped by the vacuum pump 1 flow. The buffer zone is thus an intermediate zone between an upstream and a downstream region along the path of the gases conveyed by the vacuum pump 1. The buffer zone 18 is located upstream of the pumping chamber 3, as well as of the grid 12, and extends to the suction 11.

Figures 2, 3:
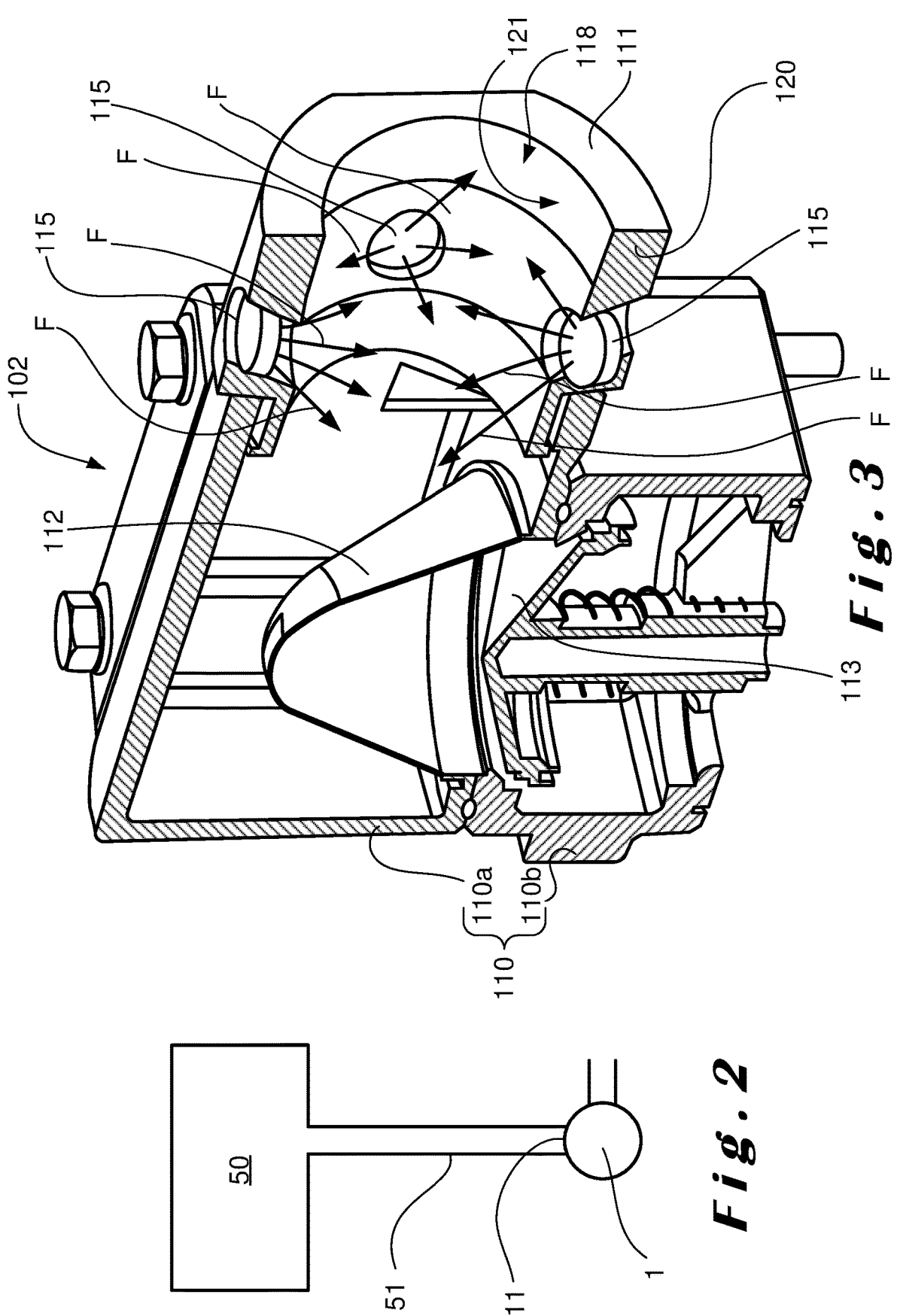
FIG. 2 is a schematic diagram of a facility that conforms to the invention and is more specifically an installation for processing and/or packaging of food products.
FIG. 3 is a perspective and cross-sectional view of an upstream subassembly of a vacuum pump according to a second embodiment of the invention.

In FIG. 2, a facility in accordance with the invention is an installation for processing and/or packaging food products. It comprises a vacuum chamber 50, the vacuum pump 1, and a connecting duct 51 that connects an opening of the vacuum chamber 50 to the suction 11 of the vacuum pump 1. In the vacuum chamber 50, food products are vacuum-packed. In the vacuum chamber 50, foodstuffs can also be processed and, if necessary, subsequently vacuum-packed.

Any contamination, for example by bacteria, upstream of the buffer zone 18 cannot pass through this buffer zone 18, to the suction 11 and to a connecting line such as the connecting line 51 connecting the vacuum chamber 50 to the vacuum pump 1 in the case of the processing and/or packaging installation shown in FIG. 2. In this case, the buffer zone 18 thus prevents contamination of the vacuum chamber 50 from the vacuum pump 1 by a pathogenic microorganism.

Furthermore, if viruses, e.g. from foodstuffs in the vacuum chamber 50, are carried by the sucked-in gases to the vacuum pump 1, these viruses are destroyed in the buffer zone 18 and are thus not expelled into the surrounding atmosphere via the discharge 9.

If food material from the vacuum chamber 50 is on the grid 12 after being stopped by the grid 12, it receives ultraviolet radiation from at least some of the ultraviolet light sources 15. This food material on the grid 12 is thus sanitized and cannot become a breeding ground for microorganisms and contamination of other areas such as the connecting duct 51 and the vacuum chamber 50 with such microorganisms.

An upstream subassembly 102 of a vacuum pump according to a second embodiment of the invention is shown in FIG. 3. In the following, only what distinguishes the vacuum pump according to the second embodiment of the invention from the vacuum pump 1 is described. Furthermore, when a referenced part of the vacuum pump according to the second embodiment of the invention is identical or equivalent to a referenced part of the vacuum pump 1, its reference is constructed by adding 100 to the reference designating this referenced part on the vacuum pump 1. In this way, in particular, the references of the grid 112 and the non-return valve 113 are created.

In addition to portions 110*a* and 110*b*, the conduit 110 of the upstream subassembly 102 includes an insert duct 120, which is provided with the ultraviolet light sources 115. The insert duct 120 includes the suction 111 of the vacuum pump according to the second embodiment of the invention. In the illustrated example, no ultraviolet light sources are provided on the portion 110*a*. When this is the case, the insert duct 120 may be mounted on a vacuum pump initially devoid of an ultraviolet light source 115 and thereby provide that vacuum pump with ultraviolet light sources 115 and a buffer zone 118.

The buffer zone 118 comprises the passageway delimited by the insert duct 120 and extends to the suction 111. The interior wall 121 of the insert duct 120 is fully illuminated by the ultraviolet light sources 115. The entire buffer zone 118 including this inner wall 121 is thus sanitized by ultraviolet radiation. Any contamination by a microorganism upstream of the buffer zone 118 cannot pass through this buffer zone 118, to the suction 111 and to a vacuum chamber when such a vacuum chamber is connected to this suction 111.

Figure 4:
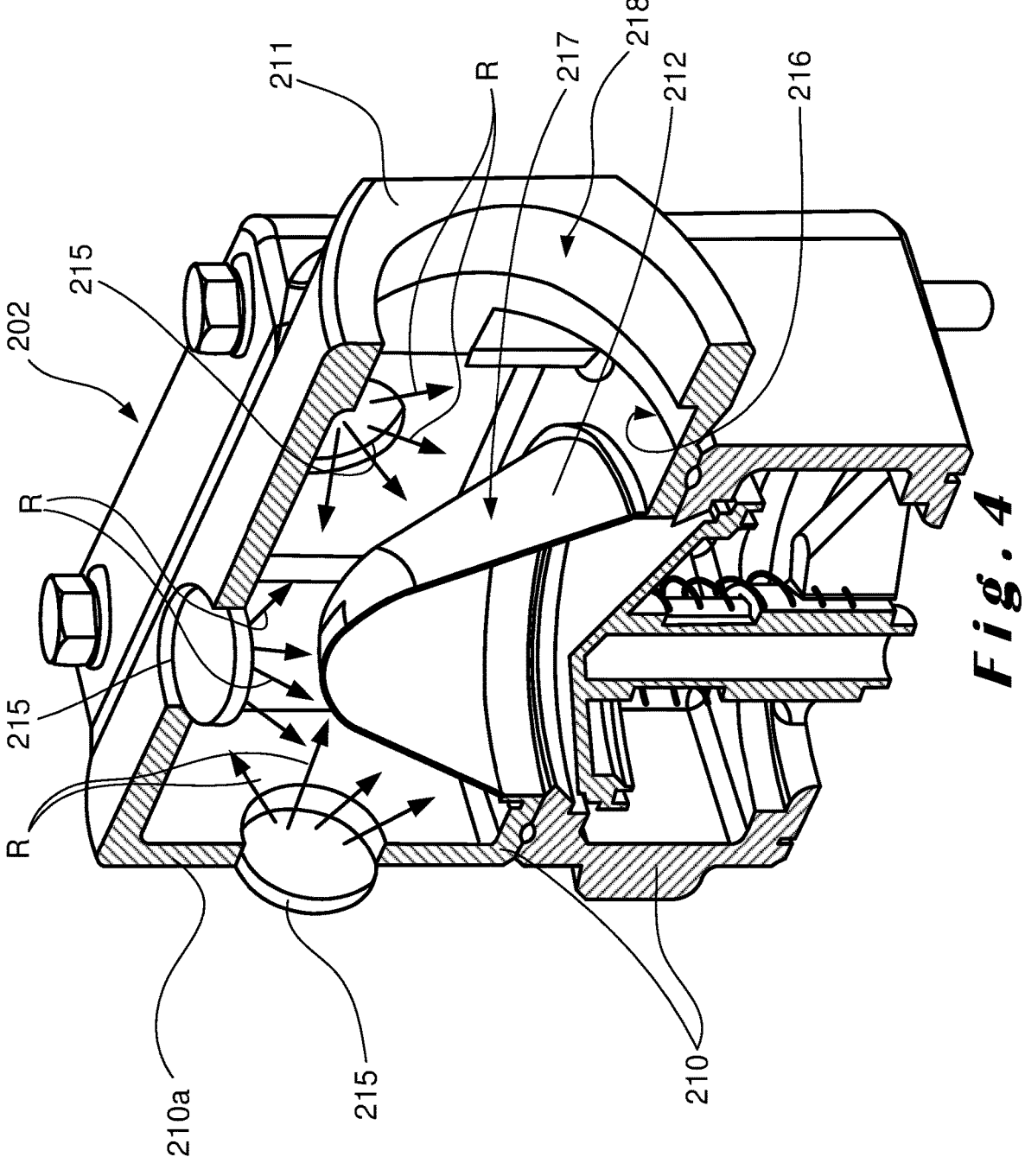
FIG. 4 is a perspective and cross-sectional view of an upstream subassembly of a vacuum pump according to a third embodiment of the invention.

An upstream subassembly 202 of a vacuum pump according to a third embodiment of the invention is shown in FIG. 4. In the following, only what distinguishes the vacuum pump according to the third embodiment of the invention from the vacuum pump 1 is described. Furthermore, when a referenced part of the vacuum pump according to the third embodiment of the invention is identical or equivalent to a referenced part of the vacuum pump 1, its reference is created by adding 200 to the reference designating this referenced part on the vacuum pump 1.

Like portion 10*a*, conduit portion 210*a* is provided with sterilization elements. Instead of being an ultraviolet light source 15, each of these sterilization elements is a heating element 215. The heating elements 215 are capable of radiantly heating the inner wall 216 of the portion 210*a* and the upstream surface 217 of the grid 212 to a temperature at which at least certain microorganisms are destroyed. For example, this temperature may be greater than about 50° C. Preferably it is higher than about 70° C. and even more preferably higher than about 120° C. The entire buffer zone 218 including the inner wall 216 and the upstream surface 217 is thus sterilized up to the suction 211. The radiation emitted by the heating elements 215 is symbolized by the arrows R in FIG. 4.

Figure 5:
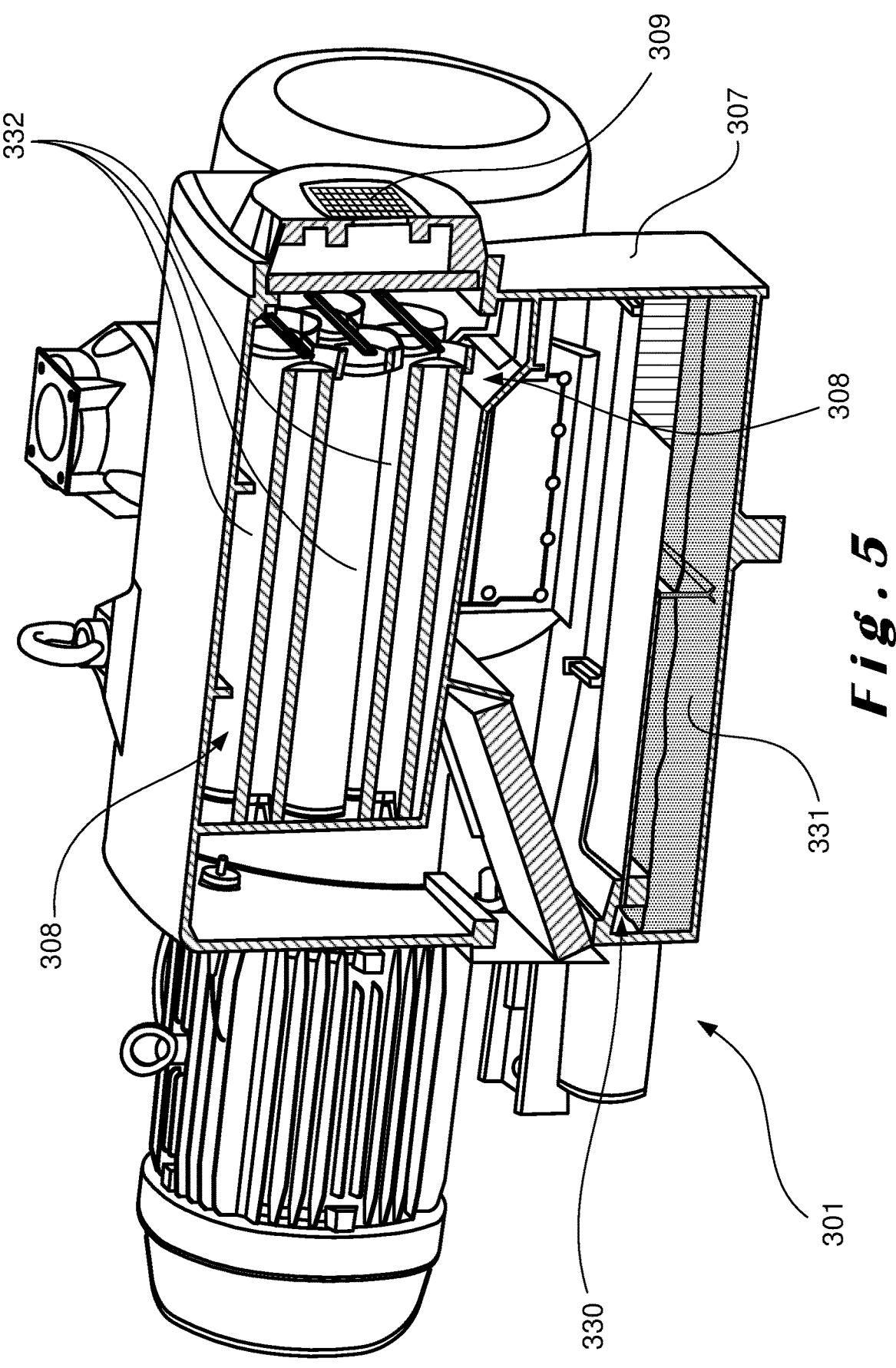
FIG. 5 is a perspective and cross-sectional view of a vacuum pump according to a fourth embodiment of the invention.

A vacuum pump 301 according to a fourth embodiment of the invention is shown in FIG. 5. In the following, only what distinguishes the vacuum pump 301 from the vacuum pump 1 is described. In addition, when a referenced portion of the vacuum pump 301 is identical or equivalent to a referenced portion of the vacuum pump 1, its reference is formed by adding 300 to the reference designating that referenced portion on the vacuum pump 1. For example, the reference of the discharge 309 of the vacuum pump 301 is formed this way.

As in the first embodiment of the invention, the lower portion of the enclosure 307 forms a tank 330 which is a lubricating oil tank and which serves to recover and store lubricating oil 331 for the vanes (not visible) of the vacuum pump 301 in a manner known per se in lubricated vane pumps. Again as in the first embodiment, the upper portion of the enclosure 307 contains an oil filter 308 provided to extract the lubricating oil 331 present in the gases after they are forced through the vanes (not visible) into the pumping chamber (not visible). The lubricating oil 331 extracted by the oil filter 308 flows by gravity to the tank 330.

The lubricating oil 331 contains a sterilizing element which is an antiseptic chemical substance that is capable of killing one or more microorganisms and/or one or more viruses. For example, this antiseptic chemical may be p-chloro-m-cresol (PCMC) or any other chemical that may be suitable as a biocide such as o-phenylphenol (OPP), iodopropynylbutyl-carbamate (IPBC), benzisothiazolinone (BIT) or bronopol. In a variant, the lubricating oil 331 may itself be, by composition, the sterilizing element. The lubricating oil 331 sterilizes a buffer zone 318 that includes the pumping chamber and the region including the filter cartridges 332 of the oil filter 308. Any viruses that may be drawn in by the vacuum pump 301 are destroyed in the buffer zone 318 and are thus not released into the surrounding atmosphere through the discharge 309.

The vacuum pump 301 may include ultraviolet light sources as in the first embodiment of the invention, in which case these ultraviolet light sources may be arranged and oriented as the ultraviolet light sources 15 are in the first embodiment or as the ultraviolet light sources 115 are in the second embodiment of the invention. The vacuum pump 301 may also include heating elements that may be arranged and oriented as the heating elements 215 are in the third embodiment of the invention. The vacuum pump may also not include an ultraviolet light source or heating elements.

In a vacuum pump not shown according to a fifth embodiment of the invention, ultraviolet light sources may be provided in an enclosure having the same function as the enclosure 307 of the fourth embodiment of the invention. In this case, these ultraviolet light sources can be provided in the lower part of the enclosure, in such a way that they can illuminate the lubricating oil and the oil tank, or in the upper part of the enclosure, for example in place of one of several oil filter cartridges.

The invention is not limited to the embodiments described above. In particular, although the vacuum pump in these embodiments is a lubricated vane pump, the invention is not limited to lubricated vane pumps. Indeed, any type of vacuum pump, lubricated or non-lubricated, may be in accordance with the invention. In particular, a vacuum pump conforming to the invention may be selected from among a vane pump, a screw pump, a gear pump, an ejector and a lobe pump.

The invention claimed is:

1. A vacuum pump, comprising a suction, a discharge and an interior volume through which gases conveyed from the suction to the discharge by pumping of the vacuum pump are to flow, and at least one sterilization element of at least one portion of the interior volume, wherein the interior volume comprises a buffer zone adapted to be sterilized by the sterilization element(s), said buffer zone comprising a passage for all the gases conveyed by the pumping by the vacuum pump.

2. The vacuum pump according to claim 1, wherein the at least one sterilization element comprises a plurality of sterilization elements.

3. The vacuum pump according to claim 1, wherein the buffer zone extends to the suction of the vacuum pump.

4. The vacuum pump according to claim 1, further comprising at least one pumping chamber where the conveying of the gases by the vacuum pump takes place, at least a part of the passage of the buffer zone being located upstream of the pumping chamber.

5. The vacuum pump according to claim 1, further comprising a grid for filtering the pumped gases, this grid being located upstream of the pumping chamber, at least part of the passage of the buffer zone being located upstream of the grid.

6. The vacuum pump according to claim 5, wherein one upstream surface of two opposing major surfaces of the grid is sterilizable by the sterilizing element(s).

7. The vacuum pump according to claim 1, further comprising an insert duct forming the suction of the vacuum pump, this insert duct being provided with at least one said sterilization element.

8. The vacuum pump according to claim 1, wherein at least one of the sterilization elements is an ultraviolet light source.

9. A vacuum pump, comprising a suction, a discharge and an interior volume through which gases conveyed from the suction to the discharge by pumping of the vacuum pump are to flow, and at least one sterilization element of at least one portion of the interior volume, wherein at least one of the sterilization elements is an ultraviolet light source, and wherein the ultraviolet light source is one of several ultraviolet light sources included in the vacuum pump and which are able to illuminate together a whole portion of an inner wall delimiting and surrounding the passage of the buffer zone.

10. The vacuum pump according to claim 1, wherein at least one of the sterilization elements is a heating element.

11. A vacuum pump, comprising a suction, a discharge and an interior volume through which gases conveyed from the suction to the discharge by pumping of the vacuum pump are to flow, and at least one sterilization element of at least one portion of the interior volume, wherein the vacuum pump is a lubricated pump comprising a pumping chamber where the conveying of gases by the vacuum pump takes place, as well as lubricating oil present in the pumping chamber, the lubricating oil being or comprising at least one of the sterilization elements.

12. The vacuum pump according to claim 11, wherein at least one of the sterilization elements is or comprises an antiseptic chemical substance.

13. An installation for processing and/or packaging food products, comprising a vacuum chamber and the vacuum pump according to claim 1, the suction of said vacuum pump being connected to the vacuum chamber.

* * * * *